(12) United States Patent
Huang

(10) Patent No.: US 6,418,779 B1
(45) Date of Patent: Jul. 16, 2002

(54) STRUCTURE OF OXYGEN SENSOR

(75) Inventor: Chien Nan Huang, Pa Te (TW)

(73) Assignee: Ceradex Corporation (TW)

( * ) Notice: Subject to any disclaimer, the term of this patent is extended or adjusted under 35 U.S.C. 154(b) by 66 days.

(21) Appl. No.: 09/589,763

(22) Filed: Jun. 9, 2000

(51) Int. Cl.[7] .............................................. G01N 27/46
(52) U.S. Cl. ....................... 73/23.31; 73/23.2; 73/31.05
(58) Field of Search ............................... 73/23.2, 23.31, 73/31.05, 31.06, 23.32; 204/424

(56) References Cited

U.S. PATENT DOCUMENTS

| | | | | |
|---|---|---|---|---|
| 2,940,041 A | * | 6/1960 | Jacobson ..................... | 73/23.2 |
| 3,960,692 A | * | 6/1976 | Weyl et al. .................. | 204/428 |
| 4,040,930 A | * | 8/1977 | Dillon ......................... | 204/429 |
| 4,187,163 A | * | 2/1980 | Steinke et al. .............. | 73/23.31 |
| 4,210,510 A | * | 7/1980 | Grimes ....................... | 204/428 |
| 4,320,378 A | * | 3/1982 | Taniguchi et al. ......... | 73/31.05 |
| 4,668,477 A | * | 5/1987 | Nishio et al. .............. | 73/31.05 |
| 4,882,029 A | * | 11/1989 | Eickmann ................... | 204/400 |
| 5,336,390 A | * | 8/1994 | Busack et al. .............. | 204/424 |
| 6,164,120 A | * | 12/2000 | Friese et al. ............... | 73/31.05 |

* cited by examiner

Primary Examiner—Hezron Williams
Assistant Examiner—Michael Cygan
(74) Attorney, Agent, or Firm—Troxell Law Office PLLC

(57) ABSTRACT

An oxygen sensor used with an electronic control unit in a car and having a metal housing formed by a front cap, a rear cap and an intermediate barrel and secured by a lock nut. A probe is mounted in the metal housing to detect an amount of oxygen in exhaust gas from the car and to produce a voltage signal indicative of the amount of oxygen detected. A terminal transmits the voltage signal from the probe to an electronic control unit in the car. The oxygen sensor includes a water sealing plug fastened to the rear cap, a first ceramic holder element, a second ceramic holder element, an electrode washer connected between the first ceramic holder element and the probe, and a metal compression spring mounted inside the intermediate barrel to push the ceramic holder elements apart. A lead-out wire connected to the bottom end of the metal compression spring transmits the voltage signal from the probe to the electronic control unit in the car.

2 Claims, 4 Drawing Sheets

STRUCTURE OF OXYGEN SENSOR

BACKGROUND OF THE INVENTION

The present invention relates to an oxygen sensor with an electronic control unit in a car to detect the amount of oxygen in exhaust gas, and more particularly to an improved structure of oxygen sensor, which dissipates heat efficiently, and has means to absorb shocks during its operation.

A car is generally equipped with an oxygen sensor, which detects the amount of oxygen in exhaust gas, and produces a voltage signal indicative of the amount of oxygen detected. The voltage signal from the oxygen sensor is provided to an electronic control unit in the car for analysis, enabling the electronic control unit to adjust the air/fuel ratio automatically. A conventional oxygen sensor is generally comprised of a metal housing, a spring mounted inside the housing, a cylindrical ceramic holder supported on the spring inside the housing, a probe installed in the cylindrical ceramic holder inside the housing to detect the amount of oxygen in exhaust gas from the car and to produce a voltage signal indicative of the amount of oxygen detected, and a terminal connected to the probe and extended out of the housing for transmitting the voltage signal from the probe to the electronic control unit in the car. The spring is provided to absorb shocks only, and not used for signal transmission. Further, because the cylindrical ceramic holder is a solid member, it consumes much material, and provides no space for quick dissipation of heat.

SUMMARY OF THE INVENTION

It is one object of the present invention to provide an oxygen sensor, which has a heat dissipation space on the inside for quick dissipation of heat. It is another object of the present invention to provide an oxygen sensor, which uses a metal compression spring to transmit signal, and to absorb shocks when transmitting signal. According to the present invention, the oxygen sensor comprises a metal housing formed of a front cap, a rear cap and an intermediate barrel and secured in shape by a lock nut, a probe mounted in the metal housing to detect of amount of oxygen in exhaust gas from the car and to produce a voltage signal indicative of the amount of oxygen detected, a terminal, which transmits the voltage signal from said probe to the electronic control unit in the car, a water sealing plug fastened to the rear cap and stopped against the intermediate barrel, a first ceramic holder element and a second ceramic holder element respectively mounted inside the intermediate barrel, an electrode washer connected between the first ceramic holder element and the probe, a metal compression spring mounted inside the intermediate barrel to push he ceramic holder elements apart, the metal compression spring having a top end stopped at the electrode washer against the probe and a bottom end extended out of the second ceramic holder element and the water sealing plug, and a lead-out wire connected to the bottom end of the metal compression spring for transmission of the voltage signal from the probe to the electronic control unit in the car. Because the metal compression spring forces the ceramic holder elements apart, a space is left between the ceramic holder elements for quick dissipation of heat.

DETAILED DESCRIPTION OF THE PREFERRED EMBODIMENT

Figure 1:
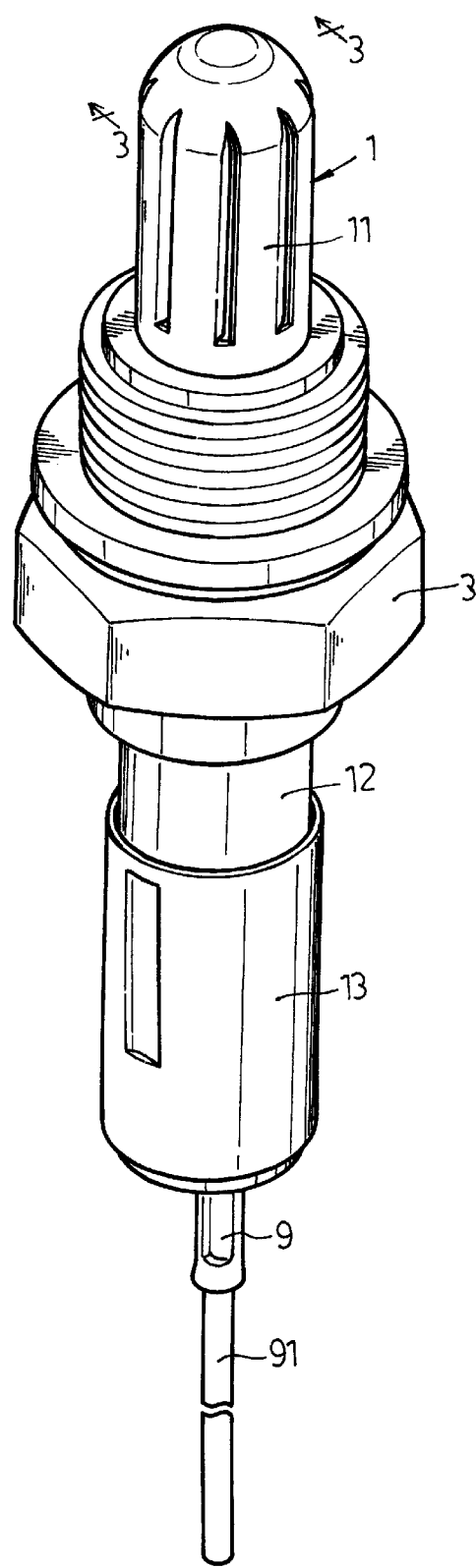
FIG. 1 is an elevational view of an oxygen sensor according to the present invention.
Figure 2:
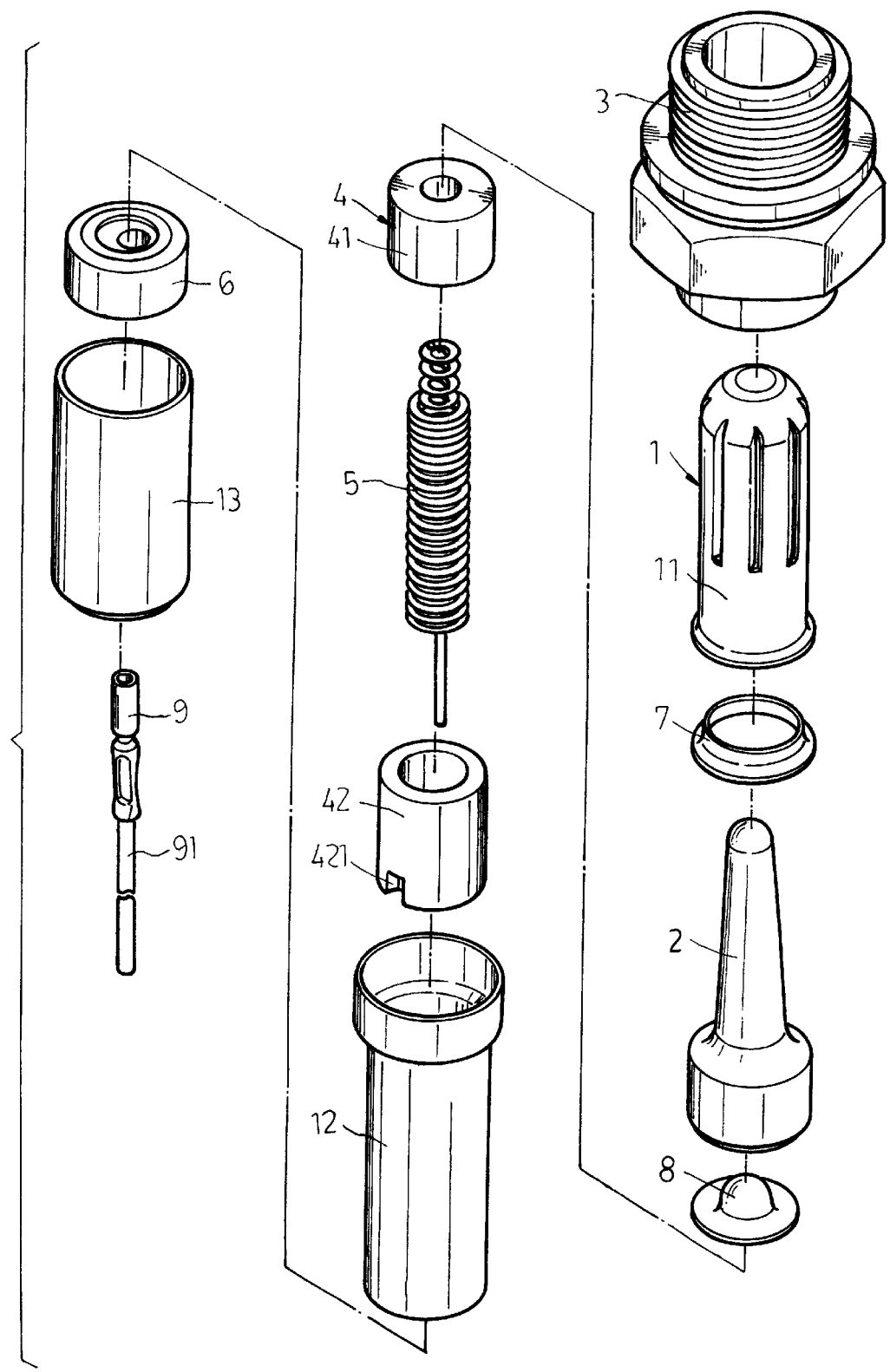
FIG. 2 is an exploded view of the oxygen sensor shown in FIG. 1.
Figure 3:
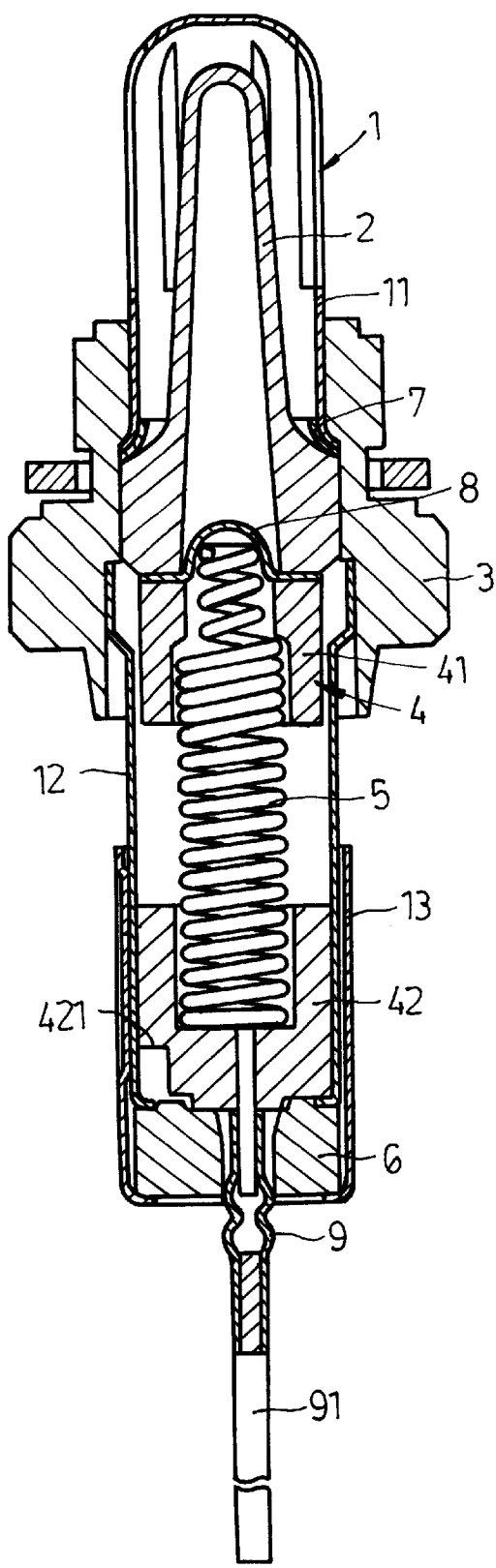
FIG. 3 is a sectional view taken along line 3—3 of FIG. 1.

Referring to FIGS. from 1 through 3, an oxygen sensor in accordance with the present invention is generally comprised of a metal housing 1, a probe 2, a lock nut 3, a ceramic holder assembly 4, a metal compression spring 5, and a water sealing plug 6. The housing 1 is comprised of a front cap 11, an intermediate barrel 12, and a rear cap 13. The front cap 11 covers the probe 2. The probe 2 is made of zirconia, which absorbs oxygen from waste gas of temperature over 300° C., and produces an electric voltage signal corresponding to the amount of oxygen absorbed.

The probe 2 has its top end inserted into the front cap 1, and its rear end inserted into the intermediate barrel 12. The lock nut 3 is mounted on the front cap 11 and fastened to the intermediate barrel 12 to secure the front cap 11 and the intermediate barrel 12 together. The ceramic holder assembly 4 and the compression spring 5 are mounted inside the intermediate barrel 12. The rear cap 13 is covered on one end, namely, the bottom end of the intermediate barrel 12. The ceramic holder assembly 4 is comprised of a front holder element 41 and a rear holder element 42 respectively mounted in intermediate barrel 12. The water-sealing plug 6 is fastened to the rear cap 13 and stopped against one end, namely, the bottom end of the intermediate barrel 12. The compressing spring 5 is mounted inside the intermediate barrel 12 to force the front holder element 41 and the rear holder element 42 apart, having a spiral top end of reduced diameter stopped against an electrode washer 8, which is retained between the front holder element 41 and the probe 2, and a straight bottom end through the rear holder element 42 and the water sealing plug 6. A terminal 9 is fastened to the straight bottom end of the compression spring 5, having a heat-resisting lead-out wire 91 suspended outside the rear cap 13.

When in use, oxygen content in exhaust hot gas from the car induces the probe 2 to produce a voltage signal corresponding to the amount of oxygen present in exhaust hot gas, and to send the voltage signal through the electrode washer 8, the compression spring 5 and the terminal 9 to an electronic control unit (not shown) for analysis, enabling the electronic control unit to adjust the air/fuel ratio subject to the level of the voltage signal.

Because the front holder element 41 and the rear holder element 42 are pushed apart by the compression spring 5, a space is left between the front holder element 41 and the rear holder element 42 for quick dissipation of heat and, for absorbing vibration waves from the compression spring 5.

Figure 4:
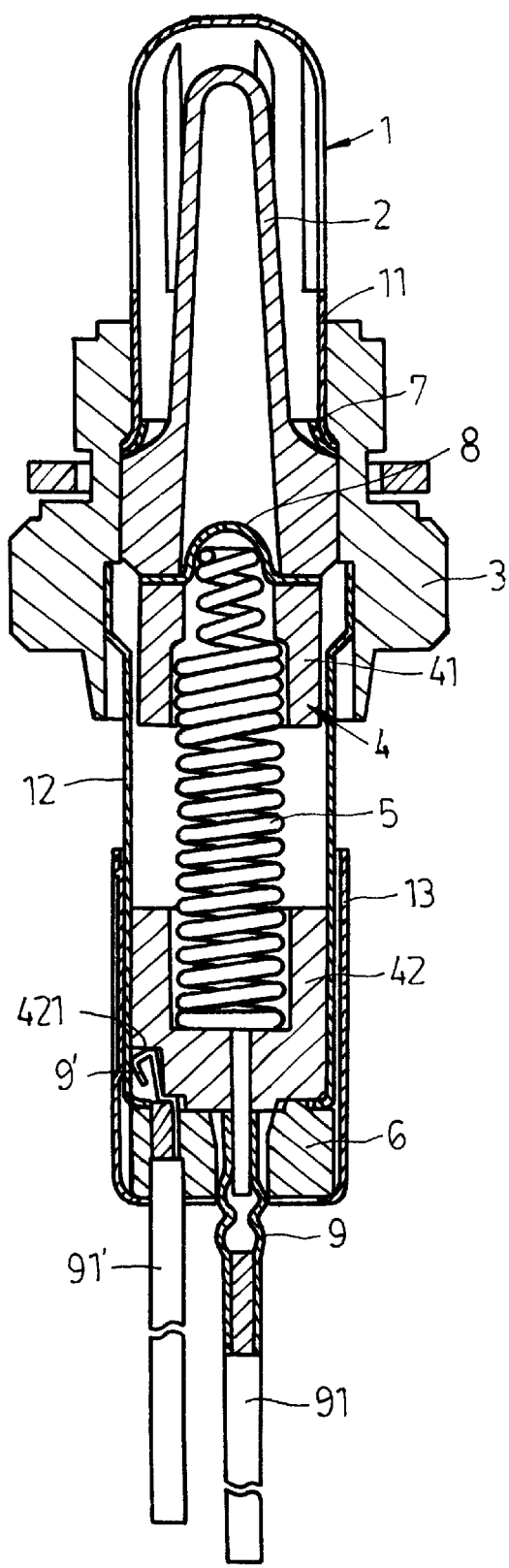
FIG. 4 is a sectional view of an alternate form of the present invention.

Referring to FIG. 4, an external electrode washer 7 is connected between the front cap 11 and the probe 2, and a metal spring plate 9' is fastened to an outside annular groove 421 on the periphery of the rear holder element 42. The metal spring plate 9' has a heat-resisting lead out wire 91 for grounding. Thus, the external electrode washer 7, the lock nut 3, the intermediate barrel 12, the rear holder element 42, the metal spring plate 9' and the lead-out wire 91 form a grounding circuit.

While only one embodiment of the present invention has been shown and described, it will be understood that various modifications and changes could be made thereunto without departing from the spirit and scope of the invention disclosed.

What the invention claimed is:

1. A structure of oxygen sensor used with an electronic control unit in a car of the type comprising a metal housing formed of a front cap, a rear cap, and an intermediate barrel connected between said front cap and said rear cap, a lock nut fastened to said front cap and said intermediate barrel to secure said front cap and said intermediate barrel together, a probe mounted in said front cap and said intermediate barrel to detect of amount of oxygen in exhaust gas from the car and to produce a voltage signal indicative of the amount of oxygen detected, a terminal extended out of said rear cap to transmit the voltage signal from said probe to the electronic control unit in the car, the improvement comprising a water sealing plug fastened to said rear cap and stopped against one end of said intermediate barrel, a first ceramic holder element and a second ceramic holder element respectively mounted inside said intermediate barrel, an electrode washer connected between said first ceramic holder element and said probe, a metal compression spring mounted inside said intermediate barrel to push said first ceramic holder element and said second ceramic holder element apart, said metal compression spring having a top end stopped at said electrode washer against said probe and a bottom end extended out of said second ceramic holder element and said water sealing plug, and a lead-out wire connected to the bottom end of said metal compression spring for transmission of the voltage signal from said probe to the electronic control unit in the car.

2. The structure of oxygen sensor of claim 1 further comprising a second electrode washer connected between said front cap and said probe, and grounding terminal means fastened to said second ceramic holder element and disposed in contact with said intermediate barrel and forming with said metal housing and said second electrode washer a grounding circuit.

* * * * *